United States Patent
Erickson et al.

(10) Patent No.: US 6,957,655 B2
(45) Date of Patent: Oct. 25, 2005

(54) APPARATUS FOR DOSAGE CONTROL

(75) Inventors: John Erickson, Plano, TX (US); Terry Daglow, Allen, TX (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 285 days.

(21) Appl. No.: 10/334,404

(22) Filed: Dec. 30, 2002

(65) Prior Publication Data

US 2004/0055649 A1 Mar. 25, 2004

Related U.S. Application Data

(60) Provisional application No. 60/412,365, filed on Sep. 20, 2002.

(51) Int. Cl.[7] ............................................. F16K 37/00
(52) U.S. Cl. ...................... 137/1; 137/614.21; 137/554; 251/129.21; 251/129.1; 251/129.15
(58) Field of Search ..................... 251/129.15, 129.21, 251/129.1, 129.09; 137/1, 614.21, 553, 554

(56) References Cited

U.S. PATENT DOCUMENTS

| | | | |
|---|---|---|---|
| 3,302,582 A | 2/1967 | Kofink ........................ 103/53 |
| 4,253,493 A * | 3/1981 | English ................. 137/625.18 |
| 4,373,527 A | 2/1983 | Fischell ...................... 128/260 |
| 4,437,815 A | 3/1984 | McMullen .................. 417/418 |
| 4,459,989 A | 7/1984 | Borkan ........................ 128/421 |
| 4,612,934 A | 9/1986 | Borkan ........................ 128/421 |
| 4,619,653 A | 10/1986 | Fischell ........................ 604/891 |
| 4,684,368 A | 8/1987 | Kenyon ....................... 604/152 |
| 4,692,147 A | 9/1987 | Duggan ......................... 604/93 |
| 4,714,462 A | 12/1987 | DiDomenico ................. 604/67 |
| 4,731,051 A | 3/1988 | Fischell ........................ 604/67 |
| 4,784,645 A | 11/1988 | Fischell ....................... 604/153 |
| 4,793,353 A | 12/1988 | Borkan ........................ 128/421 |
| 4,808,089 A | 2/1989 | Buchholtz et al. ........... 417/417 |
| 4,883,467 A | 11/1989 | Franetzki et al. ............ 604/152 |
| 4,931,050 A | 6/1990 | Idriss ....................... 604/891.1 |
| 5,012,836 A * | 5/1991 | Jacobsen et al. ......... 251/129.08 |
| 5,049,141 A | 9/1991 | Olive ....................... 604/891.1 |
| 5,085,402 A | 2/1992 | O'Dell ................... 251/129.21 |
| 5,085,563 A | 2/1992 | Collins et al. ............... 417/417 |
| 5,109,850 A | 5/1992 | Blanco et al. .............. 128/635 |
| 5,422,780 A | 6/1995 | Lignar ......................... 361/154 |
| 5,658,133 A | 8/1997 | Anderson et al. .............. 417/63 |
| 5,869,078 A | 2/1999 | Baudino ....................... 424/423 |
| 5,928,195 A | 7/1999 | Malamud et al. ............ 604/141 |
| 5,938,690 A | 8/1999 | Law et al. ...................... 607/46 |
| 6,002,964 A | 12/1999 | Feler et al. .................... 607/46 |
| 6,027,456 A | 2/2000 | Feler et al. ................... 600/554 |
| 6,048,328 A | 4/2000 | Haller et al. ................... 604/93 |
| 6,104,957 A | 8/2000 | Alo et al. ....................... 607/46 |
| 6,154,678 A | 11/2000 | Lauro .......................... 607/115 |
| 6,203,523 B1 | 3/2001 | Haller et al. .............. 604/93.01 |
| 6,228,057 B1 | 5/2001 | Vasko .......................... 604/151 |
| 6,374,624 B1 * | 4/2002 | Cholkeri et al. ......... 251/129.21 |

* cited by examiner

*Primary Examiner*—Kevin Lee
(74) *Attorney, Agent, or Firm*—Fulbright & Jaworski LLP

(57) ABSTRACT

The invention is directed to a dose control apparatus for manipulating the dosage of one or more pharmaceutical solutions emanating from an implantable drug infusion pump. The dose control apparatus has a movable core that is held in a desired position by a magnet. The apparatus has at least one coil that, when activated, motivates the core to move to a new position. The core may be held in the second position by another magnet. The apparatus may have more that one coil provide various control options. In addition, the coils may be used to determine core position or the presence and strength of an externally applied magnetic field such as that produced in an MRI. The coils may also be used to produce a magnetic field counteracting the externally applied field or to produce a degaussing field.

24 Claims, 9 Drawing Sheets

APPARATUS FOR DOSAGE CONTROL

RELATED APPLICATIONS

This application claims priority of U.S. patent aplication Ser. No. 60/412,365, filed Sep. 20, 2002 entitled: "Programmable Flow Controller", and is incorporated herein by reference in its entirety.

TECHNICAL FIELD OF THE INVENTION

This invention, in general, relates to an implantable drug delivery system. More specifically, this invention relates to a dose control system and valves used to manipulate the delivery rate of a pharmaceutical solution.

BACKGROUND OF THE INVENTION

Implantable drug infusion therapy has been used to treat various ailments including pain management and diabetes. These drug pumps and delivery systems have been used to deliver pain medication, hormones such as insulin, and other pharmaceutical agents. For example, intraspinal drug delivery may be used to treat chronic pain. By utilizing these systems, pharmaceutical agents are delivered in relatively lower doses to a specific region of treatment. In this manner, full body dilution and membrane barriers are avoided. Similarly, insulin may be delivered without the inconvenience of injections.

Infusion pumps come in several varieties. Some infusion pumps are constant rate such as those driven by gas pressures or springs Others are variable rate pumps driven by hydration of an expandable substance or a variable rate pumping mechanism.

Implantable drug delivery systems have several advantages over external drug pumps, oral medications, suppositories, and injections. These implantable systems are unobtrusive, unencumbering, and typically deliver smaller doses to targeted regions. Pills, suppositories, and injections deliver large doses of pharmaceutical agents that pass through a large portion of the body to reach the treatment area. The large dilution ratio caused by this passing requires a large dose to achieve an effective concentration in the treatment area. In addition, patients must remember to administer the correct dose at the appropriate time to achieve the desired therapeutic levels of the pharmaceutical agent in the treatment area.

While external infusion pumps overcome some of the limitations of pills, injections, and suppositories, they are often cumbersome and inconvenient. These devices must typically be worn or strapped to the patient, encumbering clothing selection and presenting a risk of damage to the external pump. In addition, catheter incision points are subject to infection.

However, current versions of implantable infusion pump systems also have disadvantages. Typically, implantable infusion pump systems provide limited programmability and patient control. In addition, access to the pump system is limited. Some pump systems have a constant rate while others attempt to control flow rates by varying pump speeds or hydration rates. In the case of constant rate pumps, prescription rates are set by the selected flow restrictor and pump pressure. In the case of variable rate pumps, prescriptions are limited by the available rate settings associated with the pump.

Patients generally have no control over the prescription. In pain management cases, this can lead to periods of under dosing and periods of unnecessary over treatment. Doctors are also limited in the selection of prescriptions and often must have an office visit with patients to adjust prescriptions. These adjustments are expensive to insurance companies, unprofitable for doctors, and inconvenient for patients.

In the case of other treatments such as insulin treatment, the required prescription varies with the behavior and environment of the patient. Insulin requirements increase with carbohydrate laden meals and decrease with activity. Excess insulin can lead to shock and low insulin can lead to excess blood sugar levels and many long-term health problems.

Another problem with implantable infusion pumps is determining actual dosage rates and predicting reservoir levels. Limited access to the pump means expensive preemptory refilling. Typical implantable infusion pumps do not maintain rate data useful in determining actual dosage schedules and reservoir levels. Therefore, doctors have difficulty predicting reservoir levels. This often leads to wasted pharmaceutical solution. Worse, the reservoir may empty and patents may suffer from a lack of treatment.

A further problem with current dose control systems lies in their method for controlling dose rates. These methods often use many mechanical parts that may wear. Further, these systems use parts that may malfunction under externally applied magnetic fields such as those of an MRI.

As such, typical infusion pumps suffer from deficiencies in providing prescription options, actual prescription rate data, and control of dosage. Many other problems and disadvantages of the prior art will become apparent to one skilled in the art after comparing such prior art with the present invention as described herein.

SUMMARY OF THE INVENTION

Aspects of the invention may be found in an apparatus for controlling the flow rate of a treatment solution. The apparatus includes a housing surrounding an enclosure. Two ports communicate with the enclosure through the housing. A magnet is associated with one port. A coil located outside the housing is associated with another port. A core or armature is located in the enclosure. The core is influenced by magnetic fields. At rest, the core may be held near the one port associated with the magnet. The coil is activated to create a stronger magnetic field to move the core from the magnet. In this manner, the core may be moved from a valve seat or closed position to an open position. Alternately, the core may be moved from an open position to a closed position. Further, the core may be moved from a closed position to another closed position, allowing fluid flow only during transition. A second magnet or second coil may be used to add control or a rest position.

A bellows may be attached to the housing in communication with the enclosure. The bellows may fill when the enclosure is in communication with an inlet port and drain when the enclosure is in communication with the outlet port. The bellows may also provide pressure or flow stability.

The coils may be used to detect the position of the core or the presence of an external magnetic field. The core may also be used to generate a magnetic field opposing the external magnetic field or a degaussing field. The apparatus may also be surrounded by Mu-metal.

Additional aspects of the invention are found in a method for controlling dosage rates of a treatment solution. The method includes the step of inducing a magnetic field with a coil, motivating a core from a magnet associated with a valve seat. The current in the coil may periodically be reversed to form a degaussing field. The method may also include measuring a response from the coil to determine the position of the core or the presence of an externally applied magnetic field. The coil may be further used to induce a field opposing the externally applied magnetic field.

As such, a dose control apparatus is described. Other aspects, advantages and novel features of the present invention will become apparent from the detailed description of the invention when considered in conjunction with the accompanying drawings.

BRIEF DESCRIPTION OF THE DRAWINGS

For a more complete understanding of the present invention and advantages thereof, reference is now made to the following description taken in conjunction with the accompanying drawings in which like reference numbers indicate like features and wherein.

DETAILED DESCRIPTION OF THE INVENTION

Implantable drug treatment therapy is useful in treating a variety of ailments such as chronic pain management, insulin-dependent diabetes, chemotherapy (systematic and targeted), Myelin treatment, and neurotransmitter treatment, among others. In each of these examples, patients could benefit from greater variety of prescriptions, more control, and accurate monitoring of reservoir levels.

For example, in the case of pain management, patients may benefit from selectively applying various doses based on need. A preset array of prescription levels would permit the patient to adjust treatment based on pain, increasing as needed and decreasing otherwise. Limits and other conditions may be established to prevent over dosing. Such a system would permit a patient to compensate for developing tolerances or advancing pain.

Patients can also benefit from having more than one pharmaceutical agent or treatment solution delivered to the treatment area. Differing rate of drug delivery for different drugs can be effective for pain management. For example, one pharmaceutical agent may be infused for low-level pain while another is introduced only during extreme pain. In this manner, tolerance development may be moderated for the stronger drugs, or rates may be varied for those that are more expensive.

Similarly, treatments such as insulin treatments may be managed more effectively with more patient control and multiple treatment solutions. For example, a patient may modify dose with activity and consumption. Further, agents with varying time-release patterns, co-factors, and supplements may be introduced with varying rates.

Figure 1A:
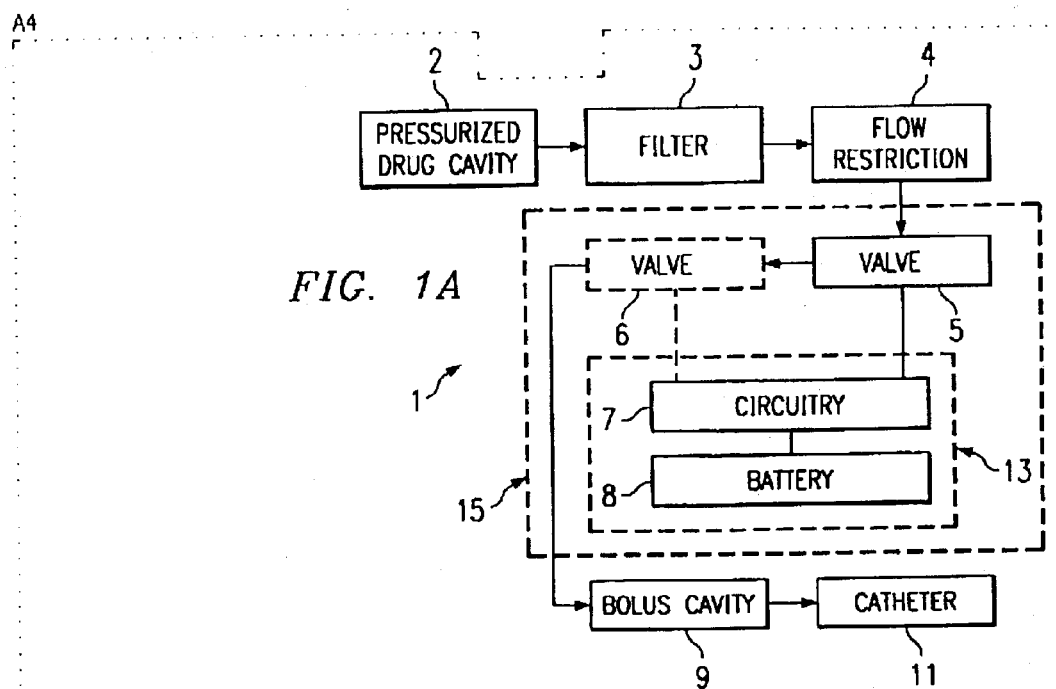
FIGS. 1A and 1B are schematic diagrams of the system, according to one embodiment of the present invention.

Such a delivery pattern is realized with a separate dose control system. FIG. 1A depicts an embodiment 1 of the present invention. A pressurized drug cavity 2 delivers a treatment solution through a filter 3 and flow restriction 4 to valves 5 and 6. However, various motivating systems may be envisaged for supplying valves 5 and 6 with treatment solutions. The circuitry 7 using energy from battery 8 manipulates the valves 5 and 6 to produce a flow rate in accordance with a prescription. However, one, two, or more valves may be used. The treatment solution may then travel through a catheter 11 to a treatment region in a patient. A bolus cavity 9 may be located inline to provide for the administering of bolus dosages.

The circuitry 7 and battery 8 comprise a dose control module and may be located separate from other elements as denoted by the enclosure 13. However, other elements such as the valves 5 and 6 may be included with the circuitry 7 and battery 8 as indicated by the enclosure 15. The bolus cavity 9 may also be enclosed with the circuitry 7 and battery 8. The drug cavity 2, filter 3, and flow restriction 4 may be located in a separate housing.

Moreover, various valve configurations may be envisioned. Valves 5 and 6 may be placed in series, parallel, or other arrangements. One, two, or more valves may be included in addition to restrictions to formulate various configurations.

Figure 1B:
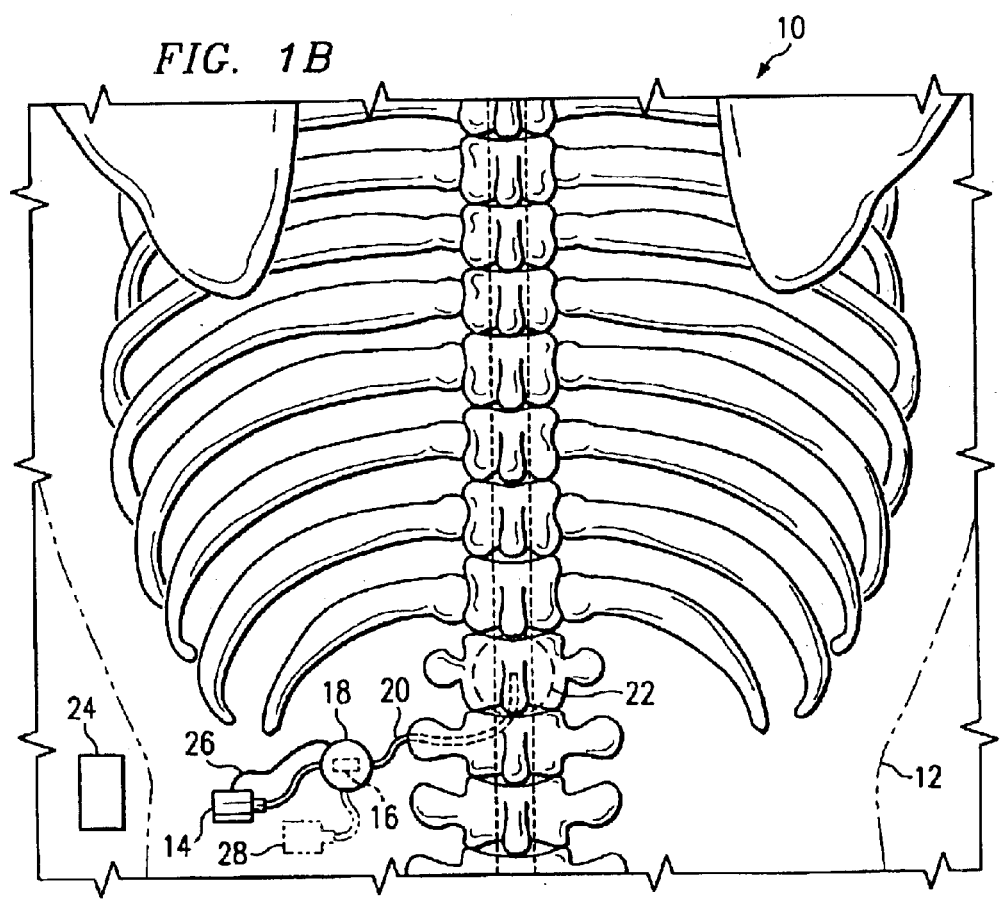

FIG. 1B shows another embodiment 10 of the present invention. FIG. 1B has an infusion pump 14 implanted in a patient 12. From the infusion pump, a catheter 20 leads through a dose control module 18 to a treatment area 22. The dose control module 18 may have a valve set 16 or other means of directing dosage. Alternately, the dose control module 18 may have a communication link 26 with the infusion pump 14 or valve set that aids in controlling dose. The system may also include an external patient control unit 24. The external patient control unit may direct the dose control module 18 to change dose rates or prescription configurations. In addition, other infusion pumps 28 may be connected with the dose control module 18 or valve set 16 such that multiple pharmaceutical solutions are delivered through the catheter 20 to the treatment area 22.

The system may be useful in treating various ailments. For example, the treatment area 22 may be intraspinal. The infusion pump 14 may deliver a morphate or other pain modifying pharmaceutical solutions through the dose control module 18, valve configuration 16, and catheter 20. In another case, the infusion pump 14 may deliver insulin through a dose control module 18 and catheter 20 to be absorbed by the bloodstream.

The patient control unit 24 may be used to modify dosage to either control pain in the case of a pain medication or control blood sugar in the case of insulin delivery. For example, the patient control unit 24 may permit the patient to select a prescription from a preset array of prescriptions which is then transmitted the dose control module 18.

A separate dose control module 18, as shown, provides an interchangeable, flexible, dose control solution for implantable drug infusion therapy. Doctors may select a dose control module based on the prescription range, while using a pump with a constant flow rate. Surgeons may also implant multiple infusion pumps and connect them to a single dose control module. In addition, doctors may establish a set of prescriptions selectable by a patient and observe actual dosage rates.

To manipulate dosage rate, the dose control module 18 sends time dependent signals to dose or flow manipulating devices such as valves and pumps, among others. A desired dosage rate may be achieved by opening a valve for a specific period of time. Alternately, the signal may open and close the valve such that a time averaged dose rate is achieved.

Figure 2:
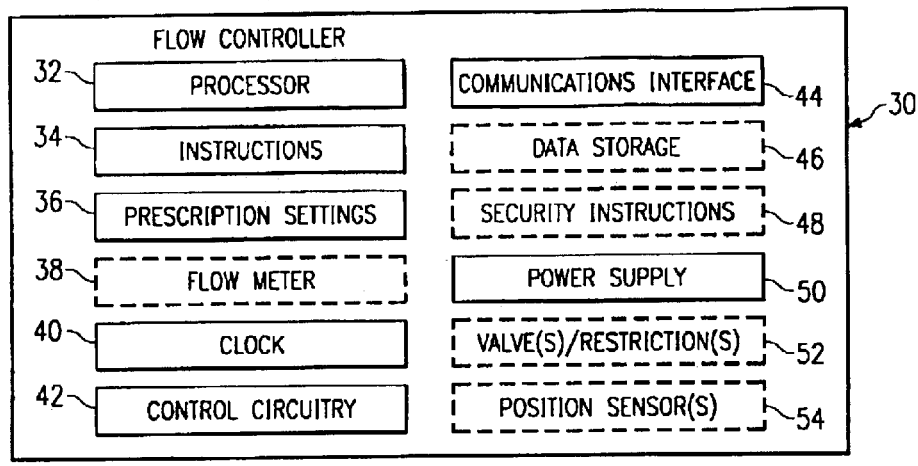
FIG. 2 is a schematic block diagram depicting a dose control module for use by the system as seen in FIG. 1A.

FIG. 2 depicts an exemplary dose control module 30. Within a hermetically sealed housing, the dose control module 30 may have a processor 32, instructions 34, prescription settings 36, a flow meter 38, a clock 40, a control circuitry 42, a communications interface 44, a data storage 46, security instructions 48, a power supply 50, dose manipulators 52, and dose manipulator state sensors 54, among others. However, these elements may or may not be included. Further, they may be housed together, separate or in various combinations, among others.

Processor 32 functions to interpret instructions 34 in view of prescription settings 36 and other data 46. The processor 32 interacts with control circuitry 42 to establish dosage rates and dose paths through the valves and restrictors 52. The instructions 34 are software instructions for implementing the various methods used by the dose control module 30 and may include instructions for establishing valve configurations, determining the dose rate, calculating effective strength, determining dosage, comparing dosage to predetermined limits, determining valve position, and communicating with other devices, among others.

The prescription settings 36 take the form of parameters associated with a prescription. These parameters may include dose rates, degradation rates, model parameters, limits, and conditions, among others. For example, a prescription setting 36 may be a dose rate of 0.8 milliliters per day, with further limits of three hours at that rate for a limit of 0.3 milliliters over any given 12 hours. In another example, the prescription rate may be expressed in $\mu$g/day with a degradation model to determine a corresponding dose rate. However, various dose rates, limits, and conditions may be associated with various therapies.

The dose control module 30 may include a flow meter 38. The flow meter 38 may take various forms including a pressure drop sensor, a rotary meter, a switch, and a force meter, among others. Alternately, the flow meter may calculate flow rates from known pump rates and valve positions.

The system may also include a clock 40. The clock 40 may be used in creating timed signals for manipulating dosage rates. The clock 40 may also be used for determining whether dosage has exceeded the predetermined limitations. Further, the clock 40 may be used to record time stamped data. The clock 40 may be used to determine time of day, time differences, and total time implanted, among others. With the clock 40 and the flow meter 38, actual dosage data may be recorded, limits and conditions tested, and reservoir levels calculated. The benefits include an understanding of dosage rates, better prediction of reservoir levels, and more accurate adherence to overdose safety limits. Additional counters may be used to count fills and other parameters.

The control circuitry 42 is used to establish valve position or dose rates. This is accomplished by selectively sending signals to dose manipulators such as valves and pumps. The processor in accordance with the instructions 34 and the prescription settings 36 directs the control circuitry to create signals, manipulating valve position to control dose rates.

The communications interface 44 may take various forms including an interface with an external computer prior to implanting, or a radiofrequency interface to external devices. With a connection to a computer, the dose control module 30 may be programmed and configured prior to implanting. Once implanted, a doctor may interface with the device to establish prescription settings 36, download or upload other data from the data storage 46, and determine reservoir levels, among other data. With a patient control unit, a patient may choose a prescription selected from a set of prescriptions preset by the patient's doctor.

The dose control module 30 includes a data storage 46. The data storage 46 may store time-stamped dose data, dosage data, other parameters associated with valves, restrictors and device configuration, calculated reservoir levels, and other data. The data storage may take the form of various RAM or flash memories, among others. The data may also be transmitted and stored on a patient control unit.

The dose control module 30 may also include security instructions 48. These security instructions can include encryption algorithms or authentication methods such as device identification numbers to limit access to the functionality of the dose control module 30. Communications with unauthorized devices may be ignored or limited in their access to alter prescriptions.

The power supply 50 may take the form of a battery. The power supply may also include a means of recharging from an externally applied RF signal. The system may also monitor the power supply 50. If the power supply 50 reaches a low level or power is lost, the system may include fail-safe electronic circuitry that could place the valves in a safe position or the valve design can default to a safe configuration prior to the loss of power. For example, a reserve power supply or capacitor may direct the closing of all valves.

The dose control module may also include dose manipulators such as valves and restrictions. These dose manipulators may be arranged in various configurations to provide a variety of dosage rates and prescription configurations. Using various valve configurations, the dose control module may also deliver more than one drug, implement bolus infusions, and permit a variety of pharmaceutical delivery rates to one or more catheters. However, the valves may also be located external to the dose control module 30.

The dose control module 30 may also include position sensors 54 for determining the position of valves or state of dose manipulators 52. Alternately, the dose control module may use signals produced by the control circuitry 42 and processed by the processor 32 to determine the valve position. For example, signal response from an inductance coil may be used to determine the position of a valve core.

Figure 3:
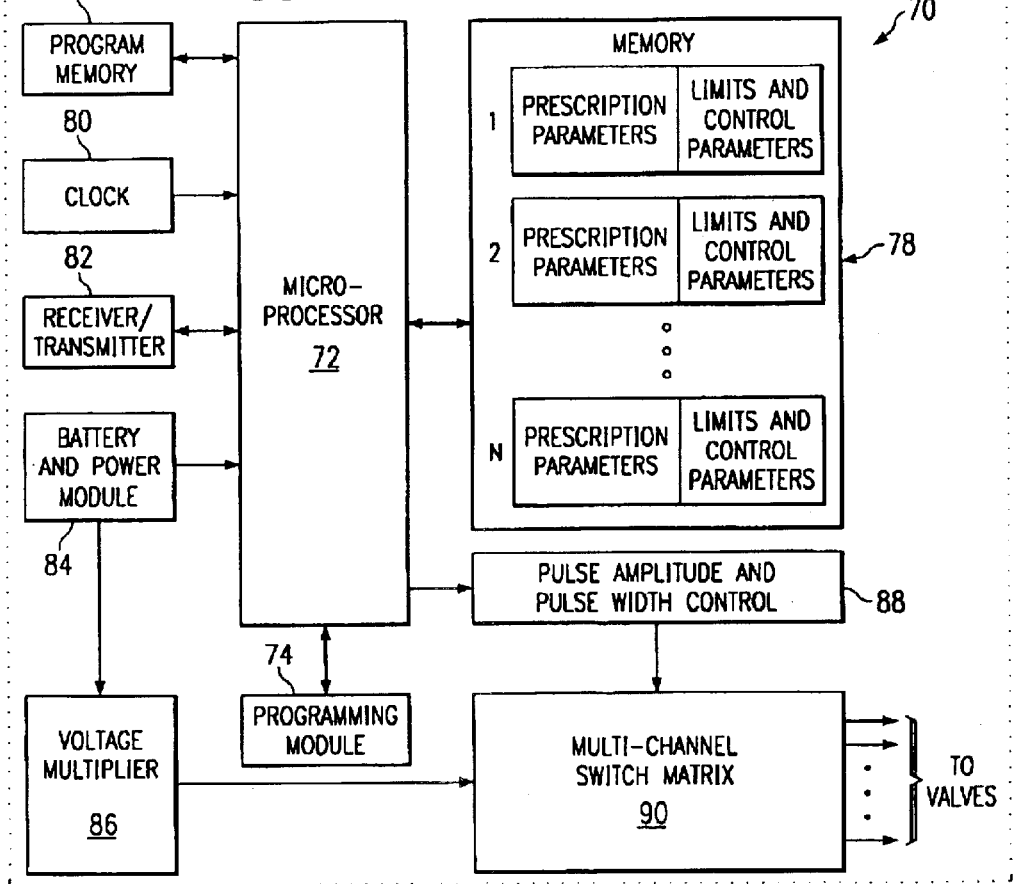
FIGS. 3 and 4 are schematic block diagrams depicting exemplary embodiments of a dose control module as seen in FIG. 2.

FIG. 3 depicts another embodiment of a dose control module 76. The dose control module 70 includes a microprocessor 72. The dose control module 70 may be programmed using a programming module 74. Instructions for the microprocessor may be stored in the programming memory 76 and prescription parameters may be stored in the memory 78. Alternately, instructions may be received through the receiver/transmitter 82.

The program memory 76 may take the form of ROM, RAM, or flash memory, among others. Similarly, the memory 78 may take the form of ROM, RAM or flash memory, among others.

The system may also include a clock 80 for time stamping data, determining whether dosage limit conditions have been met, and producing time sensitive signals, among others. For example, the clock may be used in creating an electromagnetic pulse signal for maintaining a minimum magnetic field about an inductance coil. The clock can also be used in determining a dosage ratio or total dosage for comparison with limits and conditions.

The power supply module 84 may provide power to the microprocessor. Further, it may be used on conjunction with a voltage multiplier 86 to control valve position. In accordance with the prescription parameters and the instructions stored in the program memory, the microprocessor 72 may provide electromagnetic signals to valves, directing the opening and closing of those valves using a pulse amplitude and width controller 88 and switch matrix 90.

The dose control module may be housed in a module, separate from a pump and reservoir. Valves, restrictions, and other dose manipulators may be included in the module or housed separately. In this manner, a single dose control module may manipulate dose rates associated with more than one pharmaceutical solution and/or multiple valves to achieve a selected prescription.

The patient control unit may have a circuitry similar to that shown in FIG. 3. The patient control unit may have a processor, various memories, a clock, a receiver/transmitter, a power supply, and a programming modulator interface. With these elements the patient control unit may communicate prescription selection and other data with the dose control module.

Figure 4:
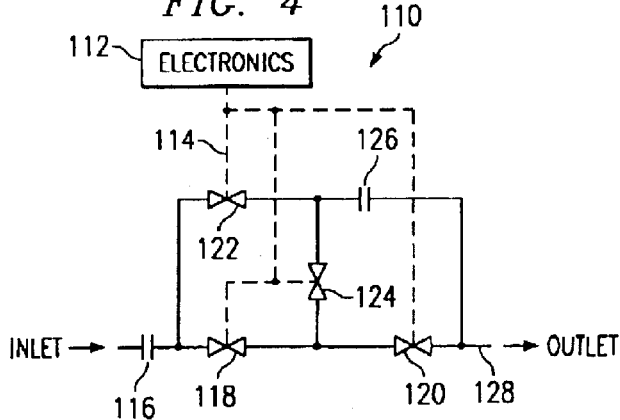

FIG. 4 depicts an exemplary valve array 110. The electronics 112 and the dose control module communicate through one or more control lines 114 to a set of valves 118, 120, 122 and 124. The system may also include various restrictors 116 and 126.

In this exemplary embodiment, a therapeutic solution enters the inlet and may pass through a restriction 116 if one is in place. The valves are configured to deliver the desired dose rate through the outlet catheter 128. The valves may be configured in parallel using valves 118 and 122. Alternately, the valves may be configured in series using valves 118 and 120. Further, the valves may be configured in various complicated arrangements.

For example, if two 0.4 ml/day valves or restrictors separated by valves are placed in parallel, the resulting flow would have a maximum of 0.8 ml/day depending on the pump's capacity. On the other hand, the two valves or restrictors, in series would yield a lower flow rate.

Various configurations of valves and restrictors may be envisioned. Configurations may be envisioned that permit multiple therapeutic solution inlet points delivered to a single outlet, a single inlet to multiple outlets, and various combinations. Further configurations may be envisioned that permit a variety of dose options.

Figure 5:
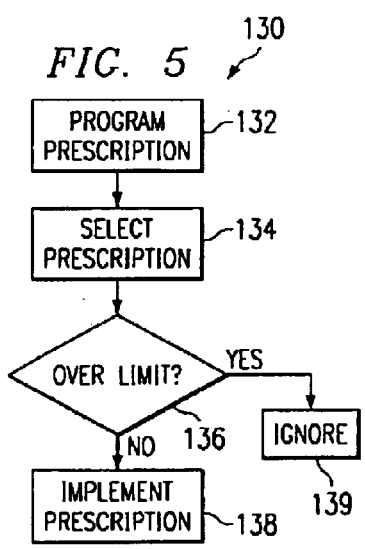
FIGS. 5, 6, 7, and 8 are block flow diagrams depicting exemplary methods for use by the dose control module of FIG. 2.

FIG. 5 depicts an exemplary method for use by the dose control module. The method 130 begins with the establishment of a prescription or a set of prescriptions as seen in block 132. A surgeon may establish the prescriptions before or during the surgery using a computer. Alternately, the prescriptions may be established using an RF signal device after implanting. Access to the prescriptions may be varied by time of day, reservoir levels, bolus limitations, time-out periods, and average dose limits, among others.

Once implanted, the dose control module may permit the patient to select a prescription as seen in block 134. The selection of a prescription may, for example, be to initiate a bolus injection or select from a preset set of dosage rates. The patient may activate an external control unit and transmit the desired prescription parameters to the dose control module. The prescription parameters may include dose type, dose rate, drug type, limits, and duration, among other data.

The dose control module then determines whether the selected prescription is permissible as seen in block 136. Permissibility of a prescription may be a function of dosage limits, reservoir availability, and other limits and conditions included as part of the prescription set by a doctor. If the selected prescription provides dosage rates above the prescribed limit, the system ignores the selection as seen in block 139. Alternately, if the selection is permissible, the dose control module may implement the prescription as seen in block 138. To implement the prescription, the dose control module configures the valves in accordance with the prescription settings and other parameters.

Figure 6:
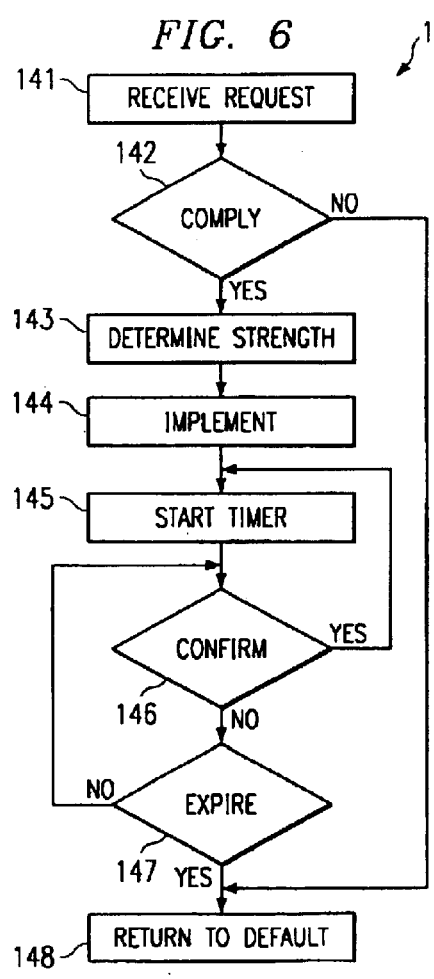

FIG. 6 depicts another exemplary method 140. The dose control module receives a request for a new dosage as seen in block 141. The request may be received from a patient control unit or may be preprogrammed in the dose control module. The dose control module may test the request to determine whether it complies with dosage rules as seen in block 142. These dosage rules may include limits on average dose, periods between bolus treatment, and time of day restrictions, among others. If the request does not comply, the control unit may apply a default dosage as seen in block 148.

However, if the request does comply, the system may determine how to implement the dose. This determination may include determining the strength of the treatment solution in the reservoir as seen in block 143. The strength of solution may be affected by degradation, initial concentration, time in place, and other factors. For example, the dose control unit may determine the effective concentration of a treatment solution using a degradation model and then implement a flow rate that provides the requested dose as seen in block 144. However, the determination may be made before the compliance test or at other steps in the method.

Once the dose is implemented, the dose control module monitors the length of time the dose has been implemented. This may include storing a start time and comparing a clock value to the start time. Alternately, a timer may be started as seen in block 145.

Periodically, the system may confirm the request with an external patient control unit as seen in block 146. If the patient control unit confirms the request, the timer may be restarted or a new initial time recorded.

However, if the patient control unit does not respond or the unit does not confirm the dose, the dose control module may determine whether time has expired on the does as seen in block 147. If time has not expired, the dose control module may again seek to confirm the dose. If the time expires, the module may return to a default dose as seen in block 148.

Figure 7:
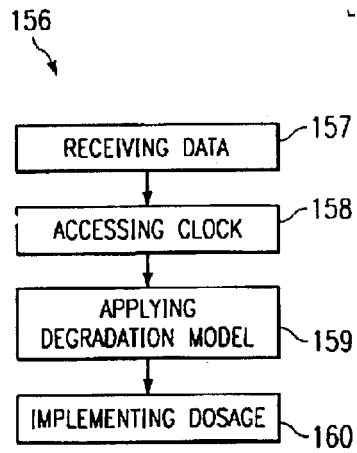

FIG. 7 is another exemplary method 156 for use by the system. Data is received as seen in block 157. The clock is then accessed in block 158. The clock may provide a time and date for comparison with stored times or may provide a period since refilling. These times are then applied in a degradation model as seen in block 159. However, various parameters may be used in a degradation model including model constants, stored values, and reservoir condition data, among others. From the degradation model, the system may determine a strength of the treatment solution and implement a dosage as seen in block 160. For example, application of the degradation model may provide an effective strength of the treatment solution. A flow rate may be implemented that complies with the dose.

Figure 8:
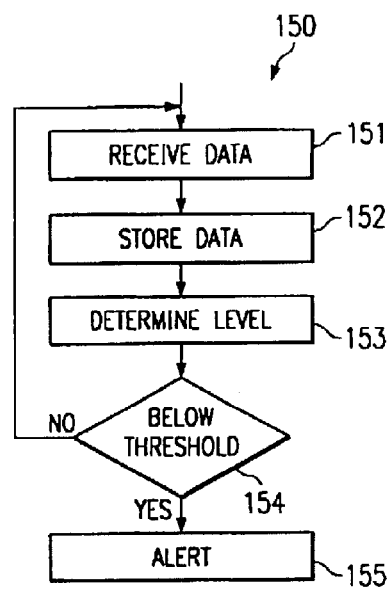

FIG. 8 depicts a further method 150 for use by the system. A patient control unit receives data from a dosage control module as seen in block 151. The data may include flow rate or dosage data, parameters, and prescription options, among others. The data is stored in the patient control unit as seen in block 152. Operations may then be performed on the data. With flow rate data, the patient control unit may determine a level in a treatment solution reservoir as seen in a block 153. If the level is below a threshold as determined in block 154, the patient control unit may alert a patient or medical professional as seen in block 155. However, various operations may be envisaged and the result of these operations may be transmitted and/or stored in the dosage control module.

Figure 9A:
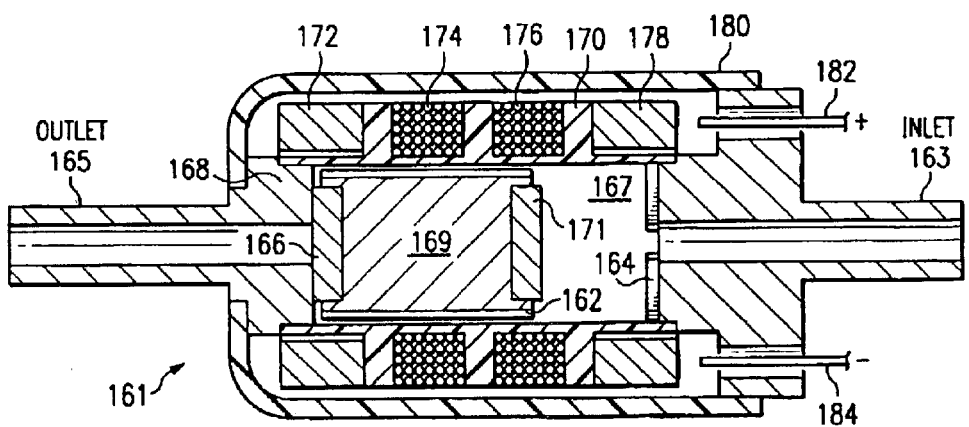
FIGS. 9A, 9B, 9C and 9D are schematic diagrams depicting an exemplary embodiment of a valve for use in the system as seen in FIG. 1A.
Figure 9B:
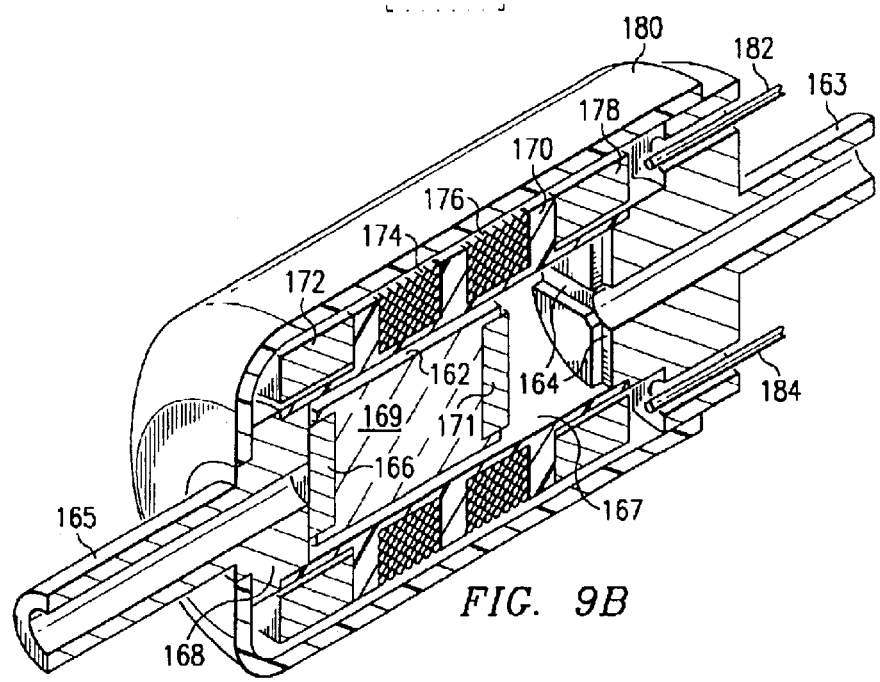

FIGS. 9A, 9B, 9C and 9D depict an exemplary embodiment of a valve for use by the system. The valve is enclosed in a hermetically sealed exterior housing 180. An interior housing 170 surrounds an interior enclosure or chamber 167. The valve has an inlet port 163 and an outlet port 165. The inlet port 163 and outlet port 165 connect to the interior chamber 167. Inside the interior chamber 167 is a core, armature, or plunger 169, which may include magnetic material. The core 169 may include channels 162 that permit fluid to pass by the core 169 when the core is in the open position. The core 169 also includes heads 171 and 166. FIGS. 9A and 9B depict the valve in a closed position. In the closed position, head 166 rests on seat 168, effectively blocking the outlet 165.

Outside of the interior chamber 167 and interior housing 170 reside magnets 178 and 172 and coils 174 and 176. When an electromagnetic signal is directed through connectors 182 and 184 and wires (not shown) to the coils 174 or 176, one of the coils 174 or 176 induces a magnetic field causing movement of the core 169. For example, if the core 169 is in the closed position as shown in FIGS. 9A and 9B, the coil 176 may be activated, inducing a magnetic field which draws the core 169 away from magnet 172 and into the open position. The core 169 may be held in the open position by magnet 178 once the coil 176 is deactivated.

The hermetically sealed exterior housing 180 and the interior housing 170 may be made of non-magnetic material. The exterior housing 180 and interior housing 170 may be formed of mu-metal, non-magnetic titanium, ceramic, polymer, and other compounds. Mu-metal provides protection against external electromagnetic fields such as those produced by MRIs. The system may also counteract the electromagnetic fields by producing an opposing field using the coils 174 and 176.

Figure 9C:
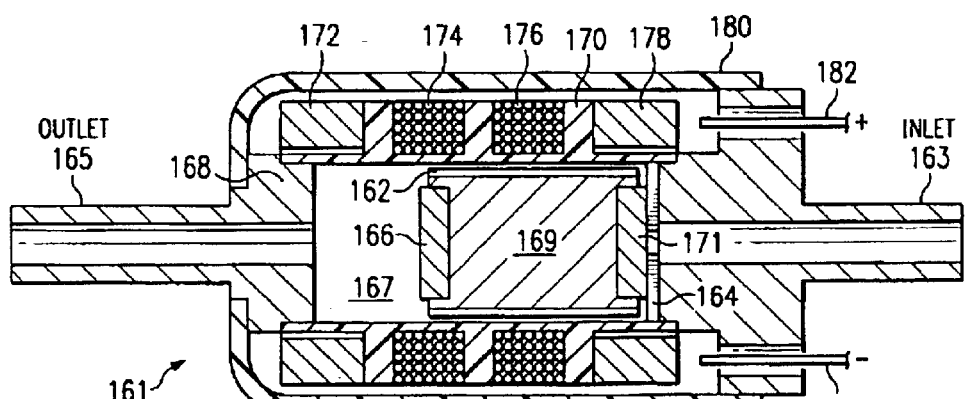
Figure 9D:
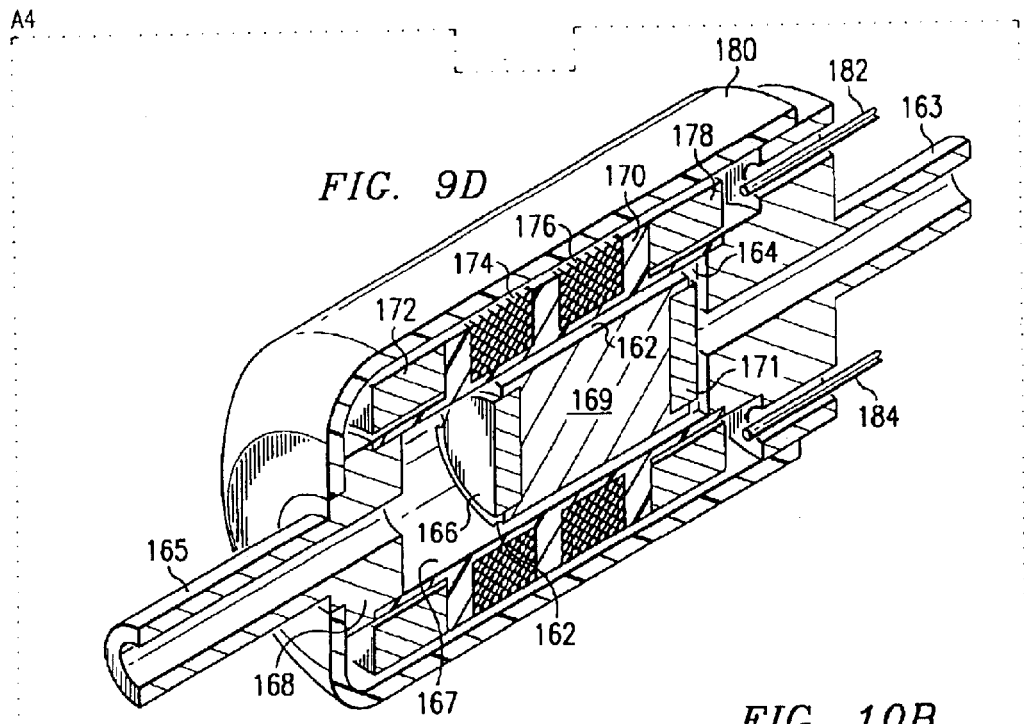

FIGS. 9C and 9D depict the valve in the open position. To move from the closed position to the open position, coil 176 may be activated creating a greater magnetic attraction near the inlet 163. The core 169 then moves towards the inlet 163. The coil 176 may then be deactivated and the magnet 178 holds the core in place. Fluid then travels through channels 162 and 164 into the chamber 169 and through the outlet 165. To close the valve, the coil 174 may be activated, creating a greater magnetic field closer to the outlet, drawing the core 169 back to the closed position. Magnet 172 holds the core in position. In this manner, the position of the core may be cycled to produce the desired dosage rate with minimum energy usage.

The permanent magnets 172 and 178 hold the core 169 in position. These permanent magnets 172 and 178 also provide a redundancy protection in the case of mechanical shock to the system. In the event of shock or change in gravitational forces, the magnets 172 and 178 hold the core in the set position. The magnets 172 and 178 also resist fluid pressures from altering the position of the valve core 169.

The seat size of the valve may also be important for reducing unwanted movement of the core. If the seat size is small enough, the pump pressure experienced by the core when proximate to the inlet port will exert a force less than that exerted by the magnet holding the core in place.

However, various configurations of seats may be envisioned. Seats may be positioned about both inlets such that fluid only flows while the core is in a transient position. In another example, the inlet and outlet may be reversed.

For the configuration shown, the pump pressure will influence the valve to stay in a closed position in the event that power is unavailable or either of the magnets is damaged. Alternately, if a fail open valve is preferred, a valve seat may be placed on the inlet and the dose channels placed about the outlet. The pump pressure would then influence the core to remain in the open position if power is unavailable.

An alternate embodiment may be seen in FIGS. 10A, 10B, 10C and 10D. In the embodiment shown in FIG. 10A, the magnet 203 is positioned about a port 192. Coils 208 and 210 may be alternately activated to move the core 198 into the open position near port 192 or into the closed position near port 194. In the closed position, a head 200 may rest on the valve seat 206, effectively closing off flow.

The core 198 may take various forms. The core 198 may be made from magnetic material. This material may include paramagnetic material. In which case, the coils and magnets would pull the core 198 into position. Alternately, the core 198 could be composed of diamagnetic material. In which case, the core 198 would be pushed into position by the magnets and coils. The core 198 may also be made from composite materials that include magnetic material such as Teflon-coated ferromagnetic materials, among others. Alternately, the core 198 may be made of a non-magnetic material with magnetic rods or a secondary core inside.

The head may take various forms. These forms may include silicone and other biocompatible materials suitable for fitting snug against a valve seat.

Figure 10A:
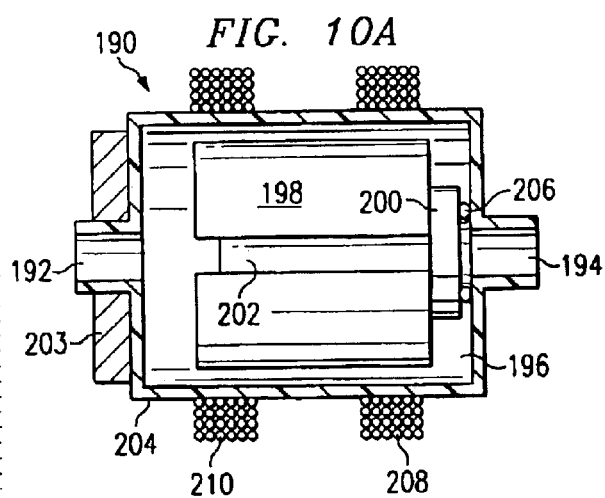
FIGS. 10A, 10B, 10C and 10D are schematic block diagrams showing another exemplary embodiment of a valve for use in the system as seen in FIG. 1A.
Figure 10B:
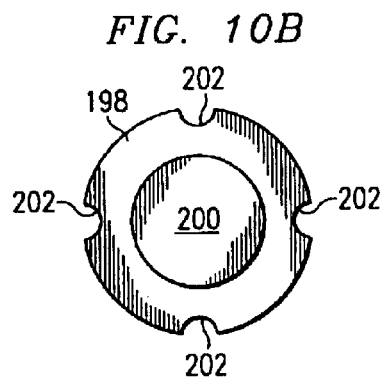
Figure 10C:
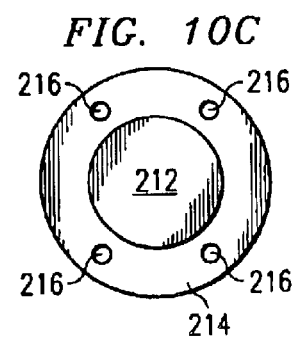

As seen in FIG. 10B, the core 198 may have channels 202 and a head 200. In the closed position the head 200 may rest against a valve seat. However, in the open position, the channels 202 may permit fluid to flow around the core 198 and through the outlet. FIG. 10C shows an alternate embodiment in which the channels 216 may be drilled through the core 214. In this case, the core 214 has a head 212 that rests on the valve seat in the closed position.

Figure 10D:
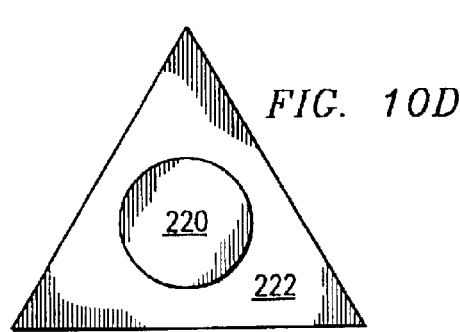

However, various seats and core styles may be envisaged. For example, FIG. 10D shows a triangular core 222 that may be positioned in a cylindrical chamber. The triangular core may have a head 220 that rests on a valve seat effectively closing the valve. However, when open, fluid may pass around the edges of the triangle with little restriction. Alternate embodiments may include a spherical core in an enclosure with a square cross-section. In this example, the sphere may be a silicone coated ferromagnetic sphere. However, many embodiments may be envisioned.

Figure 11:
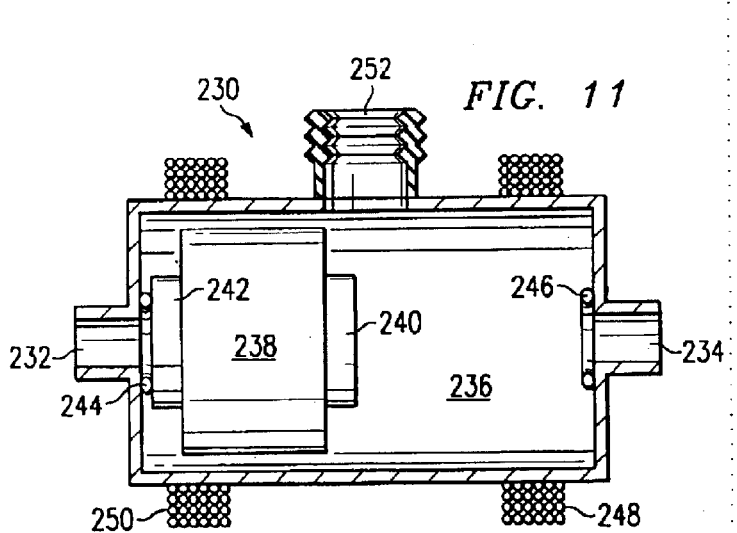
FIG. 11 is a schematic diagram depicting a further exemplary embodiment of a valve for use by the system as seen in FIG. 1A.

FIG. 11 depicts a further embodiment of the valve 230 as a core 238 in a chamber 236. The valve has a bellows 252. Coils 248 and 250 may be cycled on and off to move the core 238 through the chamber 236. When the core 238 rests on valve seat 246, the bellows 252 may fill with the pharmaceutical solution. Alternately, when the core 238 and the core head 242 rest against valve seat 244, the bellows 252 may drain through the outlet 232. One advantage to this system is that the maximum dose a patient can receive in the event of valve failure is equal to the volume of the bellows 252.

In a similar embodiment, one end of the chamber may have channels instead of a valve seat. The core 238 may be positioned at that end and permit fluid flow. In this case, the bellows will act to control pressure fluctuations or spread out the drug delivery.

Dosage control systems including the valves of FIGS. 9, 10, and 11 have another advantage in that the valve position may be determined through the response of the coils to signals. If the core is positioned near the coil, the signal will represent a different inductance than if the core is further from the coil. In this manner, the system may determine valve position and in the event of error, attempt to reposition the valve, stop flow from the pump, or alert the patient, among others.

Figure 12:
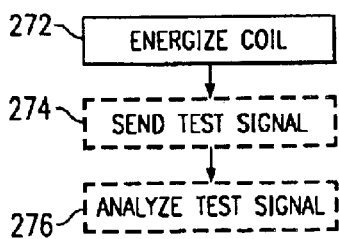
FIG. 12 is a block flow diagram depicting an exemplary method for use by the system as seen in FIG. 1A.

FIG. 12 depicts an exemplary method for operating the valve. The method 270 involves energizing the coil 272 to move the valve position into the desired position. The dose control module may then test to determine whether the core is in the correct position by sending a signal through one or the other coils as seen in block 174. The returning signal will vary in accordance with the inductance caused by the presence of the core. The dose control module may then analyze the signal as seen in block 276 to determine the position of the core. Alternately, the system may test and analyze the signal prior to energizing the coils. Further, the system may periodically test the position of the core to ensure that the valve is in the appropriate position and is functioning properly.

The coils may also be used to counteract external magnetic fields such as those produced by an MRI. The MRI may induce a current in the coils. This signal may be interpreted by a dose control module to ascertain the direction and strength of the magnetic field. A signal may then be sent to the coils to counteract or oppose the external magnetic field. In this manner, valve position may be ensured and damage to the magnets or the core prevented.

Figure 13:
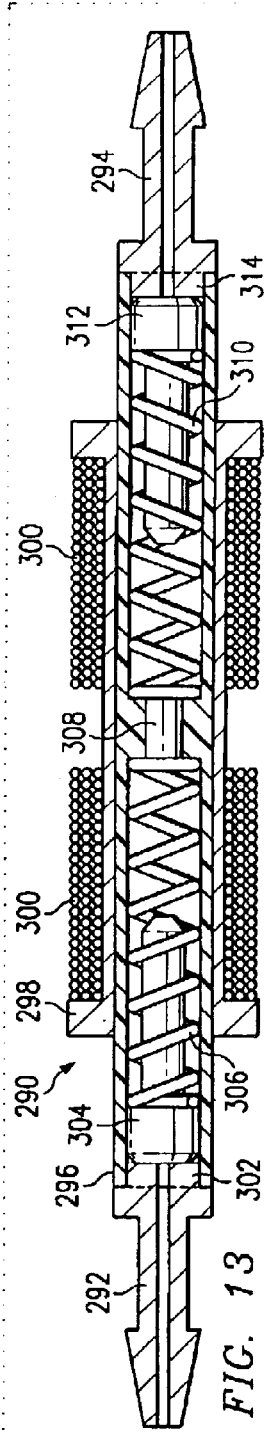
FIGS. 13, 14, and 15 are schematic diagrams depicting an exemplary embodiment of a valve for use by the system as seen in FIG. 1A.

Another valve for use by the system may be seen in FIG. 13. FIG. 13 represents a solenoid valve with dual armatures, wherein each armature may be opened by one or more coils. Valve 290 has two ports 292 and 294. These ports connect to a housing forming an interior chamber. Each port has an associated valve seat, 302 and 314. Against these valve seats may be valve heads and armatures 304 and 312, respectively. Each of these armatures is held in place by an associated spring 306 and 310, respectively. These springs, 306 and 310, may press against a spring stop 308. Alternately, they may press against separate spring stops. A spool 298 surrounds the enclosure. Coils 300 are wrapped around the spool 298. Activation of the coils 300 induces a magnetic field that draws the valve heads 304 and 312 away from their respective seats 302 and 314 and towards spring stop 308. The armatures 304 and 312 may have a common axis of movement but move in opposite directions, toward the center of valve 290.

Fluid flow occurs from one port, i.e. inlet port 292, through the interior chamber 316 and connecting chamber 320, and exists through chamber 318 and outlet port 294.

The armatures 304 and 312 may be made of magnetic material. Heads on the armatures may be made of silicone or a material capable of sealing against the valve seats. The armatures may also have channels, grooves, or holes to permit fluid flow when the head is away from the valve seat. The springs may be made of magnetic or non-magnetic material.

The hermetically sealed exterior housing 296 may be made of non-magnetic material. The exterior housing 296 may be formed of non-magnetic titanium, ceramic, polymer, and other compounds.

The valve system of FIG. 13 provides several redundancies. Having two springs and valve assemblies ensures that if one valve assembly sticks open, fluid will still be prevented from flowing by the second operational valve assembly. If the valve experiences a directional magnetic field, one valve assembly might open, however, the other would remain closed. Further, if a leak across a seat causes pressure to build in the interior of the valve, the pressure will force the valve assemblies against their seats, preventing unwanted leakage.

The design of the inlet size is also important. Smaller inlet diameters prevent leaks from the inlet port by reducing the total force against the head. This smaller force may also permit smaller spring constants to be used, reducing the opening force requirements and thus the power requirements of the coil.

Figure 14:
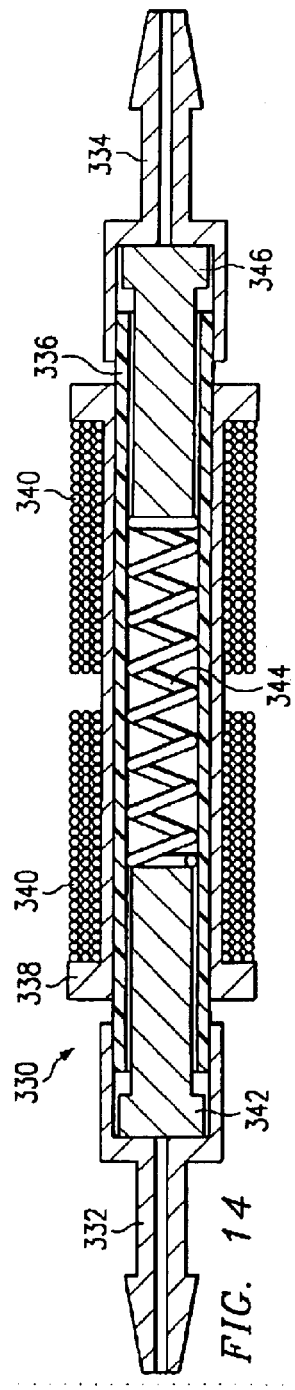

An alternate embodiment may be seen in FIG. 14 in which a common spring 344 presses the valve heads 342 and 346 against their respective seats. During the closed position, the coils 340 wrapped around spool 338 may be activated to draw the valve heads 342 and 346 inward along the axis of flow, compressing spring 344. The single spring assembly removes the double spring redundancy and hence, the valve may be advantaged by few parts for wear and tear.

Figure 15:
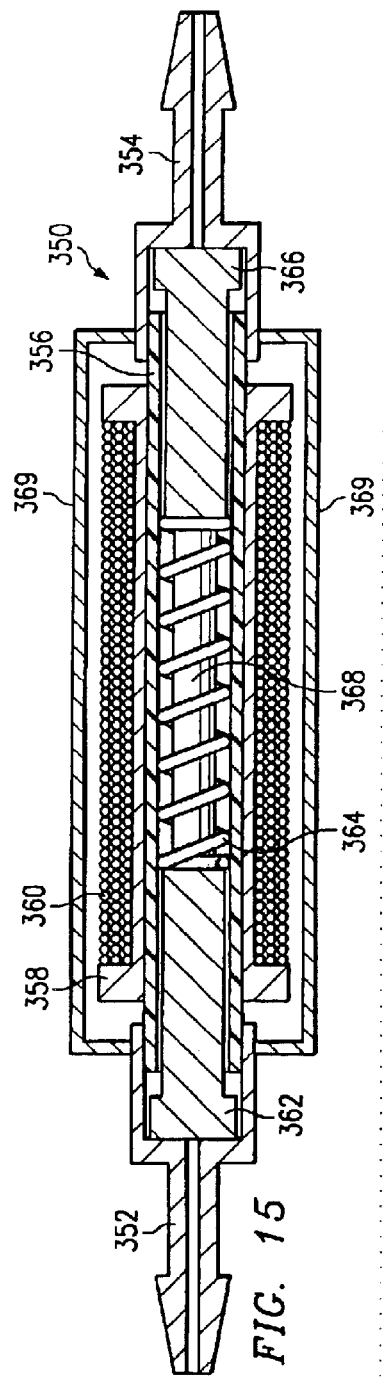

FIG. 15 depicts a further exemplary embodiment of the valve as seen in FIGS. 13 and 14. Armatures 362 and 366 are pressed against valve seat associated with ports 352 and 354 with at least one spring 364. A coil 360 may induce a magnetic force in the armatures 362 and 366 that opposes the spring 364. A core 368 is located between the armatures allowing for enough space to permit movement of the armatures sufficient for permitting fluid flow. In addition, a cover 369 is located about the coil. The cover 369 and the core 368 are made from materials that act to guide the magnetic field and in turn strengthen the effect of the coil-induced magnetic field on the armatures 362 and 366.

These valves, shown in FIGS. 13, 14, and 15, have the advantage of being redundantly in a closed position. The valves also have the advantage of alternately being in a closed position given a strong magnetic field in one direction along the axis of the valve. Such a strong magnetic field may be experienced during testing, such as an MRI.

Figure 16:
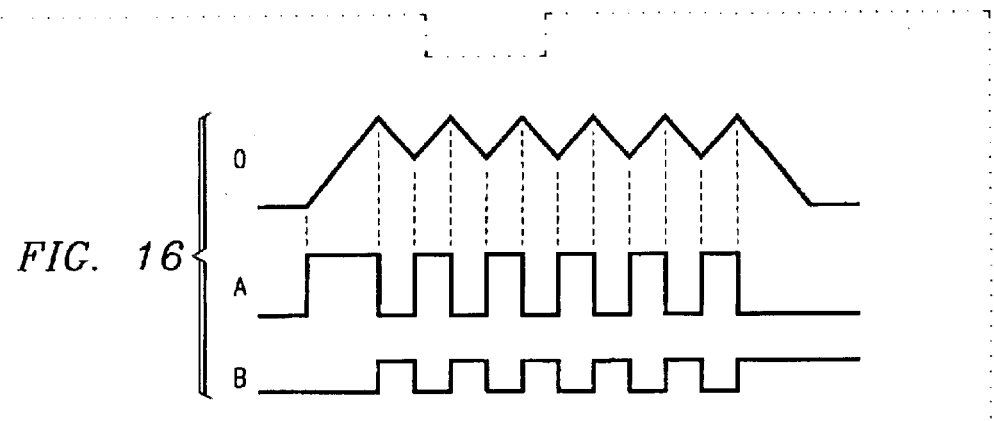
FIG. 16 is a graph depicting an inductance field resulting from a pulse signal for use by the valve as seen in FIGS. 13, 14, and 15.

Moving the valves into an open position may require more energy than keeping the valves open. This is a product of the inductance-produced electromagnetic field. To open the valves, a larger amount of energy must be applied to the coil to produce a magnetic field strong enough to open the valves. However, once the valves are open, the magnetic field may be maintained using less energy. As such, energy may be conserved by reducing the current applied to the coils or providing a timed signal to the coils, among others FIG. 16 depicts an exemplary embodiment of a timed signal. The induced magnetic field is represented by the line 0. To produce this magnetic field, a signal A is directed to the coils. To open the valve, a longer duration pulse is provided to the coils causing the magnetic field to increase. Once the valve is open, the pulse stops, causing the magnetic field to gradually decrease. During this gradual decrease, a current signal B is produced in the coil. This signal may be used for regenerating power sources or recovering energy. In this manner, power may be conserved. Once the magnetic field reaches a minimum, the signal A may produce another pulse, increasing the magnetic field. In this manner, the valve may be kept open using a minimal amount of energy. Alternately, a larger powered pulse may be used to open the valve and a constant low power signal to keep the valve open.

Figure 17:
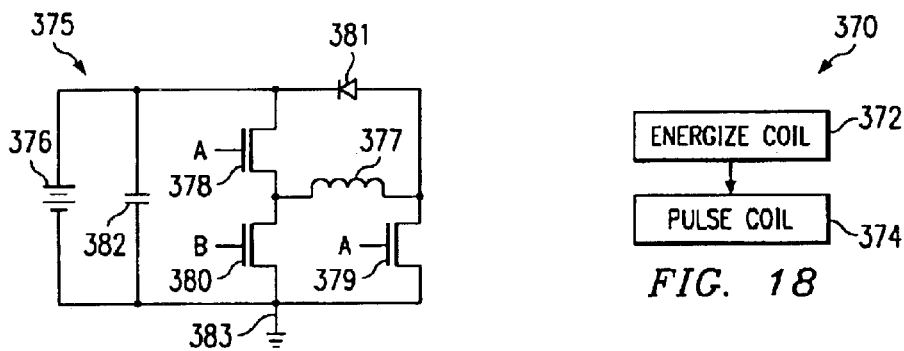
FIG. 17 is a schematic diagram of a circuit for producing the inductance field of FIG. 16.

FIG. 17 depicts an exemplary circuitry 375 for producing the signals of FIG. 16. An induction coil 377 is associated with a valve. A power source 376 is coupled with the coil 377 through switches 378, 379 and 380, and diode 381. The switches may take various forms including various transistors, four-level diodes, relays, and thyristors, among others. The circuitry may also include an energy collection circuitry 382. A controlling circuitry may be coupled to the switches. However, various modifications to this circuitry 375 may be envisaged.

If switches 378 and 379 are closed or activated, current flows through the coil 377, inducing a magnetic field. Once the field is strong enough, the valve opens. In one embodiment, the magnetic forces on the armatures in the valve overcome a spring force and open the valve. After initially opening the valve, the switches 378 and 379 are used to produce electric pulses through the coil 377 to maintain the magnetic field above a threshold value below which the valve would close or reseat.

Between pulses, the magnetic field motivates a current to flow in the same direction as that used to induce the field. If switch 380 is closed or activated, current is directed through the diode 381 toward the positive end of the power source. Alternately, energy may be collected by an energy collection circuitry 382. This circuitry 382 is depicted as a capacitor. However, it may take various forms.

Various additional switches, diodes and connections may be made to permit periodic reversal of current for producing a degaussing field with the coil 377. The system may also be grounded as seen in ground 383. However, various modifications to the circuitry may be envisaged.

Figure 18:
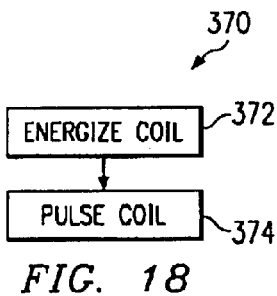
FIG. 18 is a block flow diagram depicting an exemplary method for use by the system as seen in FIGS. 13, 14, and 15.

FIG. 18 is an exemplary method for use by the system. The method 370 calls for energizing the coils as seen in block 372. This may be accomplished by providing a higher amplitude pulse or a longer pulse to produce the induced electromagnetic field. The coil may then be pulsed as seen in a block 374 to maintain the valve in an open position. The pulsing may be used to reduce the energy requirement of the system. Further, between pulses, the induced voltage and current in the coil may be used to recover energy.

The system may be subject to various strong external electromagnetic fields, as in the case of MRI testing. The valves of FIGS. 9, 10 and 11 and those of FIGS. 13, 14, and 15 may undergo these strong magnetic fields when placed in a patient. It is therefore important to counteract these strong electromagnetic fields to ensure functionality of the valve.

Figure 19:
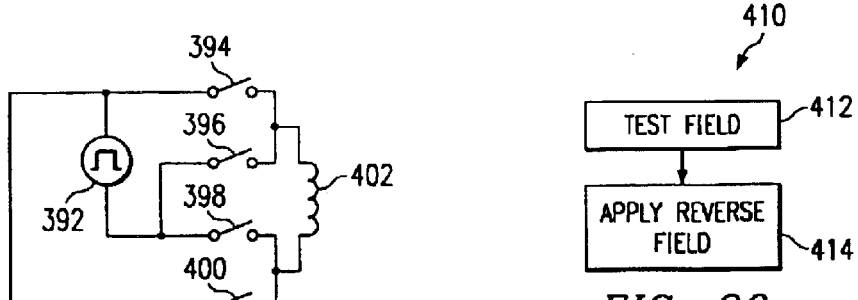
FIG. 19 is a schematic diagram of a circuit for use by the system as seen in FIG. 1A.

FIG. 19 depicts a circuit that may be used to counteract the effects of a strong unidirectional electromagnetic field or produce a degaussing field. The system may test the coil 402 to determine the direction of the electromagnetic field. Then, an opposing electromagnetic field may be produced in the coil by applying the correct voltage or current. To produce current in one direction, the switches 394 and 398 may be closed and the signal generator 392 activated. To produce current in the opposite direction, and thus an opposite electromagnetic field, switches 396 and 400 may be closed while switches 394 and 398 remain open.

This circuitry may also be used to periodically change the direction of current across a coil, effectively providing a degaussing field. The circuitry of FIG. 17 may also be modified to recover power. The circuitry of FIG. 17 may be incorporated as part of signal generator 392. Alternately, a modified circuitry may be placed about the coil 402.

Figure 20:
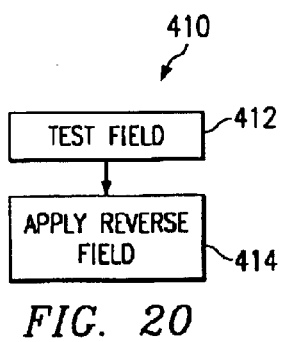
FIG. 20 is a block flow diagram of an exemplary method for use by the system as seen in FIG. 1A.

FIG. 20 depicts an exemplary method 410. In this method, the system tests for the electromagnetic field induced by the external, directional electromagnetic field. The system then applies an opposing field by sending a current in the appropriate direction through the coils as seen in a block 414.

In this manner, an external electromagnetic field may be counteracted. For the dual-head solenoid type valve, a strong unidirectional field would attempt to open one side while exerting excess pressure on the other side. Neutralization of the field would ensure valve closure, reduce wear on valve parts, and prevent magnetizing the armatures. For the movable core valve, a strong unidirectional magnet field may place the core in an undesired position, damage the permanent magnets and magnetize the core. Here too, the coils may be used to neutralize the field. Simultaneously, some of an induced current in the coils could be used to regenerate power.

Both valve types may also benefit from a reverse current periodically applied to the coils. The reverse current would cause a degaussing of magnetism and prevent residual buildup of magnetism in either the core or the armatures. Such a reverse current may be produced by the circuit of FIG. 19.

As such, a dose control module and valves are described. In view of the above detailed description of the present invention and associated drawings, other modifications and variations will now become apparent to those skilled in the art. It should also be apparent that such other modifications and variations may be effected without departing from the spirit and scope of the present invention as set forth in the claims which follow.

What is claimed is:

1. An apparatus for controlling dosage rates of at least one treatment solution, the apparatus comprising:

a valve housing surrounding an interior chamber, the valve housing having a first and second port, each port having an opening establishing communication with the interior chamber;

a core located within the interior chamber, the core comprising magnetic material;

a first magnet associated with the first port; and a first coil, the first coil operable to induce an electromagnetic field of sufficient strength to move the core from the first magnet, wherein the direction of current flow in the coil is periodically reversed to form a degaussing field.

2. The apparatus of claim 1, further comprising:
a valve seat associated with the first port, the core operable to seal against the valve seat and prevent fluid flow.

3. The apparatus of claim 1, further comprising:
a valve seat associated with the second port, the core operable to seal against the valve seat and prevent fluid flow.

4. The apparatus of claim 1, further comprising:
a second magnet associated with the second port, the second magnet holding the core proximate to the second port once the core is moved by the first coil.

5. The apparatus of claim 1, further comprising:
a second coil associated with the first port, the second coil operable to induce an electromagnetic field strong enough to attract the core to the first magnet.

6. The apparatus of claim 1, wherein the core comprises channels, the channels permitting fluid flow through the interior chamber when the core is in an open position.

7. The apparatus of claim 1, wherein the core has a cross-sectional shape differing from a cross-sectional shape of the interior chamber.

8. The apparatus of claim 1, wherein a signal is sent through the first coil to determine a position of the core.

9. The apparatus of claim 1, wherein a signal induced by an external electromagnetic field is transmitted from the first coil.

10. The apparatus of claim 1, wherein a signal is sent through the first coil inducing an electromagnetic field opposing an external electromagnetic field.

11. The apparatus of claim 1, further comprising a bellows in communication with the interior chamber, wherein the bellows allow for regulation of the volume of solution delivered.

12. The apparatus of claim 1, wherein the direction of current flow in at least one coil is periodically reversed.

13. An apparatus for controlling dosage rates of at least one treatment solution, the apparatus comprising:
a valve housing surrounding an interior chamber, wherein a component of the interior chamber is composed of biocompatible materials, the valve housing having a first and second port, each port having an opening establishing communication with the interior chamber;
a core located within the interior chamber, the core comprising magnetic material, the core operable to alternately form a seal with a valve seat associated with the first port or a valve seat associated with the second port;
a first magnet associated with the first port;
a second magnet associated with the second port;
a first coil associated with the first port, the first coil operable to induce an electromagnetic field of sufficient strength to move the core from the second magnet; and
a second coil associated with the second port; the second coil operable to induce an electromagnetic field of sufficient strength to move the core from the first magnet.

14. The apparatus of claim 13, wherein the core comprises channels, the channels permitting fluid flow through the interior chamber when the core is in an open position.

15. The apparatus of claim 13, wherein the core has a cross-sectional shape differing from a cross-sectional shape of the interior chamber.

16. The apparatus of claim 13, wherein a signal is sent through at least one coil to determine a position of the core.

17. The apparatus of claim 13, wherein a signal induced by an external electromagnetic field is transmitted from at least one coil.

18. The apparatus of claim 13, wherein a signal is sent through at least one coil inducing an electromagnetic field opposing an external electromagnetic field.

19. The apparatus of claim 13, wherein the direction of current flow in at least one coil is periodically reversed.

20. The apparatus of claim 13, further comprising a bellows in communication with the interior chamber, wherein the bellows allow for regulation of the volume of solution delivered.

21. A method for controlling dosage rates of at least one treatment solution, method comprising:
inducing a magnetic field using a coil, the magnetic field motivating a core from the influence of a first magnet associated with a first valve seat to the influence of a second magnet associated with a second valve seat; and
periodically reversing the direction of current flow through the coil to form a degaussing field.

22. The method of claim 21, further comprising:
measuring a response from the coil to determine the position of the core.

23. The method of claim 21, further comprising:
measuring a response from the coil to determine the presence of an externally applied magnetic field.

24. The method of claim 23, further comprising:
inducing in the coil a magnetic field opposing the externally applied magnetic field.

* * * * *